(12) United States Patent
Ware et al.

(10) Patent No.: US 8,969,641 B1
(45) Date of Patent: Mar. 3, 2015

(54) ISOMERIZATION OF TETRAHYDROTRICYCLOPENTADIENES TO MISSILE FUEL

(76) Inventors: Richard E. Ware, Aston, PA (US);
Edward J. Janoski, Havertown, PA (US); Abraham Schneider, Overbrook Hills, PA (US)

(*) Notice: Subject to any disclaimer, the term of this patent is extended or adjusted under 35 U.S.C. 154(b) by 0 days.

(21) Appl. No.: 05/720,308

(22) Filed: Sep. 3, 1976

(51) Int. Cl.
*C07C 5/22* (2006.01)
(52) U.S. Cl.
USPC ............... 585/373; 585/14; 585/22; 585/360; 585/362; 585/371; 7/372; 7/374
(58) Field of Classification Search
CPC .. C07C 5/2253; C07C 13/64; C07C 2527/126
USPC ............. 585/14, 22, 360, 362, 371, 372, 373, 585/374
See application file for complete search history.

(56) References Cited

U.S. PATENT DOCUMENTS

| | | | | | |
|---|---|---|---|---|---|
| 3,002,829 | A | * | 10/1961 | Kolfenbach et al. | 585/22 |
| 3,221,071 | A | * | 11/1965 | Stahly | 585/23 |
| 3,381,046 | A | * | 4/1968 | Cohen et al. | 585/22 |
| 3,864,178 | A | * | 2/1975 | Rudy et al. | 149/109.6 |

\* cited by examiner

*Primary Examiner* — In Suk Bullock
*Assistant Examiner* — Bradley Etherton
(74) *Attorney, Agent, or Firm* — McCarter & English

(57) ABSTRACT

Tetrahydrotricyclopentadienes are isomerized to a low pour point, high energy missile fuel. Aluminum trichloride is the catalyst and an inert chlorinated hydrocarbon solvent is present. The mole ratio of $AlCl_3$ to the diene is in the range between from about 0.005 to about 1.0. The isomerization temperature is in the range from between about $-20°$ C. to about $25°$ C.

10 Claims, No Drawings

US 8,969,641 B1

ISOMERIZATION OF TETRAHYDROTRICYCLOPENTADIENES TO MISSILE FUEL

The invention herein described was made in the course of or under a contract thereunder with the United States Air Force Systems Command.

BACKGROUND OF THE INVENTION

This invention relates to the isomerization of tetrahydrotricyclopentadienes, hereinafter referred to as THTCPD. More particularly the invention relates to the preparation of an isomeric mixture from THTCPD. Still more particularly the invention relates to the catalytic isomerization of THTCPD.

The resulting isomeric liquid mixture can be used as a low pour point, high energy missile fuel. Such fuels can be used in either jet or rocket propulsion. Jet propulsion includes a jet engine which can be used for a missile, an aircraft and others and includes the three basic types, i.e., ramjet, turbo-jet and pulse jet. The term rocket generally refers to a device containing its own oxygen or oxidizing agent. An article in Aviation Week and Space Technology, Jan. 26, 1976, pages 111-113, discloses some of the high density hydrocarbon fuels that are under consideration as missile fuels.

U.S. Pat. No. 3,381,046 discloses the treatment of endo-tetrahydrodicyclopentadiene with an acidic reagent to effect isomerization to the corresponding exo-isomer. This patent also discloses generally that a Lewis acid, such as aluminum chloride, can be used to isomerize endo-tetrahydrodicyclopentadiene to its exo-form. However, it cautions that the isomerization can proceed beyond the exo-diene to form undesirable compounds.

SUMMARY OF THE INVENTION

Solid THTCPD is isomerized using anhydrous aluminum trichloride ($AlCl_3$) admixed with an inert chlorinated paraffin solvent. Use of anhydrous hydrogen chloride is optional. The isomerization temperature is in the range between from about $-20°$ C. to about $25°$ C. The resulting liquid mixture of THTCPD isomers has a low pour point, a high volumetric heat of combustion, and a high density. Thus, the mixture can be used as a missile fuel. Surprisingly the isomerization occurs without the rapid destruction of the aluminum chloride by formation of a complex.

DESCRIPTION

Solid THTCPD, a $C_{15}H_{22}$ and having a C/H atomic ratio of 0.682, is generally believed to have the following structure:

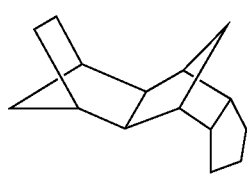

(I)

As a result of the isomerization liquid THTCPD isomers are formed. It is believed that some of formed isomers have the following structures:

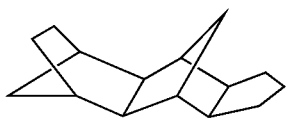

(II)

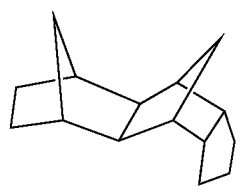

(III)

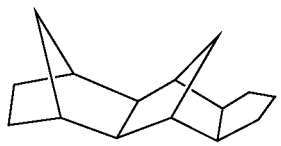

(IV)

Structure I is endo-exo-endo THTCPD; structure II is an endo-exo-exo isomer; structure III is an exo-exo-endo isomer and structure IV is an exo-exo-exo isomer.

While the THTCPD feed can contain other similar hydrocarbons, such hydrocarbons should not adversely effect the isomerization or the catalyst. Further the similar hydrocarbons should not adversely influence the desired resulting properties of the isomerized mixture. Thus, for optimum results the feed consists essentially of THTCPD which itself can be a mixture of THTCPD isomers.

The catalyst used to isomerize the THTCPD is anhydrous $AlCl_3$. The amount of $AlCl_3$ present is sufficient to control the reaction so no undesirable coproducts are formed, and depends upon the amount of THTCPD present. The mole ratio of $AlCl_3$ to THTCPD is in the range between from about 0.005 to about 1.0 and a preferable range is between from about 0.05 to about 0.3. Any material which could adversely effect the $AlCl_3$'s effectiveness r, during the isomerization should not be present. For example, the presence of hydroxylic compounds such as water, alcohol or oxygen from air could deactivate the $AlCl_3$.

Optionally, anhydrous HCl can be used to minimize or suppress the deactivation of $AlCl_3$ resulting from formation of $AlCl_3$ complex. Such a reduction in activity would be economically undesirable. Thus the amount of HCl used would be effective to enhance the reaction rate. The HCl can be added to the process by various means, for example, by passing HCl gas through the liquid mixture of THTCPD and solvent. All or some of the gas will dissolve in the mixture. The amount of HCl gas present can vary substantially; it can be far in excess of that necessary to saturate the liquid mixture or it could be substantially less than that necessary to saturate the mixture. A more operative range of HCl present is between from about 1000% to about 5% of an amount necessary to saturate the liquid mixture. a preferable range is between from about 200% to about 10% of that necessary to saturate the mixture.

An inert chlorinated paraffin liquid is used as a solvent. Since the reaction is mildly exothermic the liquid can serve as a heat sink. The liquid can also facilitate the handling of the contacting mixture and the resulting product. The liquid should not adversely react with the feed, product or $AlCl_3$. Suitable inert solvents include chlorinated paraffins such as methylene dichloride ($CH_2Cl_2$), tetrachloroethane, pentachloroethane, and others. Also the inert solvent serves as a dissolving medium for the hydrogen chloride. As to the amount of solvent used, excessive amounts can decrease the reaction rate and thus adversely effect the economics of a commercial operation. However, typically the weight ratio of the amount of solvent to the amount of THTCPD is in the range between from about 0.5 to about 1.5.

The isomerization temperature needs to be controlled between a narrow range. The lower limit can be controlled by the freezing point of the solvent and/or the rate of the reaction. While the reaction can proceed at a very low temperature the rate could be so slow as to be commercially unattractive. Thus, generally the lower temperature limit is about −20° C. with about −10° C. preferred. The upper limit is controlled by the formation of undesirable products which adversely effect the properties of the resulting missile fuel. Also if the reaction rate is too rapid at an elevated temperature an uncontrolled exotherm could result. Thus, generally the upper temperature limit is about +25° C. with about +20° C. preferred. It is also believed that a temperature in the range between from about −20° C. to 25° C. minimizes the formation of a $AlCl_3$ complex.

The pressure can vary substantially, however, economic consideration will favor a more limited range. Typically, the contacting will occur at atmospheric pressure. However, if a temperature is used which is greater than the boiling point of any solvent present then it might be advantageous to use a higher pressure to prevent the solvent from boiling away.

The properties of the resulting isomerized mixture can vary substantially depending upon the amount of isomerization that occurs. It can depend, in addition to the composition of the initial mixture on how much of each of the particular isomer of THTCPD is present. Typically the resulting isomerized mixture will have a density (20/4° C.) in the range between from about 1.044 to about 1.02 with a range between from about 1.044 to about 1.03 preferred. Since pour point is also a property to be considered for a missile fuel the resulting mixture can have a pour point of less than 0° F. and preferably less than −20° F. The net heat of combustion will be in the range between from about 156,000 BTU/gallon to about 159,000 BTU/gallon with at least 157,000 BTU/gallon preferred. As to viscosity, the isomeric mixture will have a kinematic viscosity @ 100° F. in the range between from about 15 cst to about 20 cst.

To obtain an isomerized mixture having a density, pour point and viscosity which make it useful as an additive for a high density fuel for an air-breathing missile, the reaction time or contacting time should be sufficient to obtain the desired properties. Sufficient time depends in part on the amount of the diene isomerized, the amount of stirring, the amount of $AlCl_3$ used, and HCl used, if any, the configuration of the vessel containing the reaction or contacting mixture, and other variables. The amount of isomerization can be monitored during the process by measuring, for example, the viscosity, thus when the desired amount of isomerization has been obtained, the reaction can be stopped.

After the reaction has been stopped, the solvent can be removed. If the solvent has a relatively low boiling point it can be easily boiled off. After the solvent is removed the $AlCl_3$ and hydrocarbon tars, if any, can be easily separated, for example, by decantation. The tars and $AlCl_3$ together are often referred to as sludge. With the separation of the sludge, any unreacted feed can be separated; if it is necessary or desirable to separate the unreacted feed. Then a washing of the isomeric mixture would remove any remaining $AlCl_3$. Other means to recover the isomeric mixture from the solvent and sludge are operative. However, leaving the sludge in place in a reactor after removing the hydrocarbon phase, the sludge, fortified if necessary with an additional small quantity of fresh $AlCl_3$, can be used for isomerization of subsequent batches of THTCPD.

The following examples illustrate embodiments of the present invention.

Examples

In run 1 the isomerization of THTCPD was accomplished in the following manner. In a glass reactor 13.5 grams of THTCPD were dissolved in 13.5 grams of methylene dichloride. The contents of the reactor were chilled to 0° C. and then 1.2 grams of $AlCl_3$ were added to the reactor. The resulting mixture was maintained at 0° C. while agitated for one hour. Then another one gram of $AlCl_3$ was added and mixture continued to be maintained at 0° C. while agitated for an additional half hour. The reaction was stopped by rapidly boiling off the methylene dichloride and as soon as it was gone two layers formed. The lower brown layer contained the sludge, i.e., a hydrocarbon tar and $AlCl_3$. The upper almost water-like hydrocarbon material was separated from the lower layer, and then water washed and neutralized with caustic. The yield and properties of the resulting isomeric mixtures are reported in the accompanying Table I as well as the date from runs 2 and 3. The latter runs were conducted in a similar manner as run 1 except that the reaction time was longer.

Comparison of runs 1, 2 and 3 indicate that as the time of isomerization increased the solid material was converted to a liquid having a good pour point of −50° F. Improvements in viscosity were also observed. Relatively minor decreases in density and net heat of combustion were also observed.

TABLE I

ISOMERIZATION OF THTCPD

| Run | Reaction Time (hrs) | Yield[1] | Pour[2] Point °F. | Density | Net Heat of[3] Combustion | Kinematic Viscosity, cst. 0° F. | 100° F. |
|---|---|---|---|---|---|---|---|
| 1 | 1.5 | 71 | +30 m.p. | 1.0434 | 159,250 | Solid | — |
| 2 | 3.5 | 90 | −50 | 1.0397 | 157,210 | 457 | 20 |
| 3 | 5 | 80 | −50 | 1.0374 | 156,060 | 429 | 19 |

[1]Weight %, amount of trimer recovered to that of the feed
[2]Melting point of feed was 120° F.; m.p. = melting point
[3]BTU/gallon The resulting isomeric mixtures of runs 1, 2 and 3 were also analyzed by vapor phase chromatography (vpc). These results are shown in the accompanying Table II.

TABLE II

VPC ANALYSIS OF ISOMERIC PRODUCT AND FEED

| | Areas Under vpc Peaks* | | | |
|---|---|---|---|---|
| Material | 1 | 2 | 3 | 4 |
| Feed | 88.18 | 10.79 | 1.03 | — |
| Run 1 | 54.78 | 8.22 | 23.51 | 13.49 |
| Run 2 | 24.21 | 17.31 | 46.04 | 13.63 |
| Run 3 | 17.75 | 18.96 | 49.63 | 13.67 |

*Molecular weights for all peaks were determined to be 202 by mass spectroscopy.

Comparison of the vpc peaks indicate that the amount of compound 1 decreased as the isomerization time increased. It is believed that the compound of peak 1 corresponds to the aforementioned structure (I). Run 2 indicates the isomerization of peak 1 material to the other isomers represented by peaks 2, 3 and 4. It is believed that peaks 2, 3 and 4 correspond respectively to the aforementioned structures (II), (III) and (IV).

Additional isomerization runs were made and the results are shown in accompanying Table III. Runs 4-6 were performed with sufficient HCl to saturate the liquid. In runs 4-6 after isomerization, the product was distilled and a THTCPD cut was obtained having the boiling range shown. Also shown are the properties of the various THTCPD cuts.

TABLE III

ISOMERIZATION OF THTCPD

| | | | | THTCPD CUT | | | |
|---|---|---|---|---|---|---|---|
| Runs | Reaction Time (hrs) | Reaction Temperature °C. | HCl | Boiling Range °C.[2] | Density $\left(\frac{20°}{4}\right)$ | Kinematic Viscosity @ 100° F. | Net Heat of Combustion[1] |
| 4 | 11 | 0-10 | Yes | 279-301 | 1.0265 | 15.01 | 154,420 |
| 5 | 11 | 10 | Yes | 242-282 | 1.0286 | 16.04 | 154,736 |
| 6 a. | 18 | 10 | Yes | 279-296 | 1.0352 | 17.00 | 155,729 |
| b. | 18 | 10 | Yes | >296 | 1.0430 | 23.06 | 156,902 |
| 7 | 29.5 | 18-20 | No | 249-329 | 1.0372 | 20.49 | 156,030 |

[1]BTU/gallon
[2]Atmospheric pressure

Similar results will be obtained when solvents such as tetrachloroethane or pentachloroethane are used in place of methylene dichloride. Also, concentrations of AlCl$_3$, other than those shown, give analogous results.

The invention claimed is:

1. Process for isomerizing tetrahydrotricyclopentadiene comprising:
    (a) contacting tetrahydrotricyclopentadiene with anhydrous aluminum trichloride at a temperature range between from about −20° C. to about 25° C., and in the presence of an inert chlorinated paraffin solvent wherein the aluminum trichloride is present in a mole ratio of trichloride to tetrahydrotricyclopentadiene in the range between from about 0.005 to about 1.0;
    (b) continuing said contacting until isomerization of the diene is sufficient to form a low pour point, high energy missile fuel; and
    (c) recovering the missile fuel.

2. Process according to claim 1 wherein in addition the contacting occurs in the presence of an amount of anhydrous hydrogen chloride effective to enhance the rate of isomerization.

3. Process according to claim 2 wherein the missile fuel is separated from the contacting materials.

4. Process according to claim 1 wherein the missile fuel has a pour point of less than 0° C.

5. Process according to claim 4 wherein the missile fuel has a density (20/4° C.) in the range between from about 1.044 to about 1.02.

6. Process according to claim 5 wherein the contacting occurs in the presence of an amount of anhydrous hydrogen chloride effective to enhance the rate of isomerization and the aluminum dichloride is present in a mole ratio of aluminum trichloride to tetrahydrotricyclopentadiene in the range between from about 0.05 to about 0.25, and the missile fuel is separated from the contacting materials.

7. Process according to claim 6 wherein the temperature range is between from about −10° C. to about +20° C.

8. Process according to claim 7 wherein the suitable inert solvent is selected from the group consisting of methylene dichloride, tetrachloroethane and pentachloroethane.

9. Process according to claim 8 wherein the amount of anhydrous hydrogen chloride is in the range between from about 1000% to about 5% of that necessary to saturate the contacting materials.

10. Process according to claim 1 wherein sludge, from a previous isomerization of the tetrahydrotricyclopentadiene, fortified with a small quantity of fresh aluminum trichloride is used to contact and isomerize a subsequent amount of tetrahydrotricyclopentadiene.

\* \* \* \* \*